US012630809B2

(12) United States Patent
Severinov et al.

(10) Patent No.: US 12,630,809 B2
(45) Date of Patent: May 19, 2026

(54) DNA-CUTTING AGENT BASED ON CAS9 PROTEIN FROM THE BACTERIUM PASTEURELLA PNEUMOTROPICA

(71) Applicant: JOINT STOCK COMPANY "BIOCAD", Saint Petersburg (RU)

(72) Inventors: Konstantin Viktorovich Severinov, Moscow (RU); Sergey Anatolievich Shmakov, Voskresensk (RU); Daria Nikolaevna Artamonova, Moscow (RU); Ignaty Igorevich Goryanin, Moscow (RU); Olga Sergeevna Musharova, Moscow (RU); Julia Valerevna Andreeva, Moscow (RU); Tatiana Igorevna Zyubko, Sankt-Peterburg (RU); Yana Vitalievna Fedorova, Gatchina (RU); Mikhail Alekseevich Khodorkovskii, Gatchina (RU); George Evgenevich Pobegalov, Sankt-Peterburg (RU); Anatoliy Nikolaevich Arseniev, Sankt-Peterburg (RU); Polina Anatolevna Selkova, Votkinsk (RU); Aleksandra Andreevna Vasilieva, Sankt-Peterburg (RU); Tatiana Olegovna Artamonova, Sankt-Peterburg (RU); Marina Viktorovna Abramova, Sankt-Peterburg (RU)

( * ) Notice: Subject to any disclaimer, the term of this patent is extended or adjusted under 35 U.S.C. 154(b) by 1101 days.

(21) Appl. No.: 17/617,039

(22) PCT Filed: Jun. 30, 2020

(86) PCT No.: PCT/RU2020/050137
§ 371 (c)(1),
(2) Date: Dec. 7, 2021

(87) PCT Pub. No.: WO2020/251413
PCT Pub. Date: Dec. 17, 2020

(65) Prior Publication Data
US 2022/0228134 A1     Jul. 21, 2022

(30) Foreign Application Priority Data
Jun. 11, 2019     (RU) ................................ 2019118061

(51) Int. Cl.
*C12N 9/22*          (2006.01)
*C07K 14/00*         (2006.01)
*C12N 15/113*        (2010.01)

(52) U.S. Cl.
CPC ................ *C12N 9/22* (2013.01); *C07K 14/00* (2013.01); *C12N 15/113* (2013.01); *C12N 2310/20* (2017.05)

(58) Field of Classification Search
CPC .... C12N 9/22; C12N 15/113; C12N 2310/20; C07K 14/00; C12Q 1/68
See application file for complete search history.

(56) References Cited

U.S. PATENT DOCUMENTS

| | | |
|---|---|---|
| 2015/0197759 A1 | 7/2015 | Xu et al. |
| 2022/0002692 A1 | 1/2022 | Severinov et al. |
| 2022/0017896 A1 | 1/2022 | Severinov et al. |
| 2022/0064612 A1 | 3/2022 | Madera et al. |

FOREIGN PATENT DOCUMENTS

| | | | |
|---|---|---|---|
| WO | 2018/129296 A1 | 7/2018 | |
| WO | WO-2019165168 A1 * | 8/2019 | ............. C12N 15/52 |

OTHER PUBLICATIONS

Karvelis, Methods for decoding Cas9 protospacer adjacent motif (PAM) sequences A brief overview. Methods 121-122 :3-8 (Year: 2017).*
Corresponding European application No. 20823161.3 extended European search report dated Jun. 7, 2023.
Alireza Edraki et al., A Compact, High-Accuracy Cas9 with a Dinucleotide PAM for In Vivo Genome Editing.Molecular Cell. vol. 73, Issue 4, Feb. 21, 2019, pp. 714-726.e4.
Christensen H: Rodentibacter gen. nov. and new species. Apr. 10, 2019, XP09305291, Retrieved Jun. 19, 2023 from the Internet: https://rest.uniprot.org/unisave/A0A1V3K2B7?format=txt&versions=9.
International application No. PCT/RU2020/050137 International Search Report dated Nov. 5, 2020 with English translation.
International application No. PCT/RU2020/050137 Written Opinion of the International Searching Authority dated Nov. 5, 2020.

(Continued)

*Primary Examiner* — J. E. Angell
*Assistant Examiner* — Julio Washington Gomez Rodriguez
(74) *Attorney, Agent, or Firm* — Anglehart et al.

(57) ABSTRACT

The present invention describes a novel bacterial nuclease of a CRISPR-Cas9 system from the bacterium *P. pneumotropica*, as well as the use of said nuclease for creating strictly specific two-strand cuts in a DNA molecule. The present nuclease possesses unusual properties and can be used as an instrument for introducing changes at strictly specified locations in a genomic DNA sequence of single-celled and multi-celled organisms. The invention thus increases the universality of accessible CRISPR-Cas9 systems, making it possible to use Cas9 nuclease from various organisms to cut genomic or plasmid DNA in a large number of specific sites and under various conditions.

3 Claims, 7 Drawing Sheets
Specification includes a Sequence Listing.

(56)                    References Cited

OTHER PUBLICATIONS

Astrid Weninger et al., Combinatorial optimization of CRISPR/ Cas9 expression enables precision genome engineering In the methylotrophic yeast Pichia pastoris. Journal of Biotechnology. vol. 235, Oct. 10, 2016, pp. 139-149.
A. Vasileva et al., Pasteurella pneumotropica and Demequina sediminicola Cas9 orthologs characterization. Jan. 14, 2020, Found in Internet: https://2019.febscongress.org/abstract_preview.aspx? idAbstractEnc=4424170094096092094091424170. Journal of Bio-technology. DOI: 10.1016/j.jbiotec.2016.03.027. Date: Mar. 2016.
Mojica F. J. M. et al. Intervening sequences of regularly spaced prokaryotic repeats derive from foreign genetic elements //Journal of molecular evolution.—2005.—vol. 80.—Issue. 2.—pp. 174-182.
Jansen R. et al. Identification of genes that are associated with DNA repeats in prokaryotes. Molecular microbiology.—2002.—vol. 43.—Issue. 6.—pp. 1565-1575.
Brouns S. J. J. et ai. Small CRISPR RNAs guide antiviral defense in prokaryotes. Science.—2008.—vol. 321.—Issue 5891.—pp. 960-964.
Cong L, et al., Multiplex genome engineering using CRISPR/Cas systems. Science. Feb. 15, 2013;339(6121 ):819-823.

Deltcheva E. et al. CRISPR RNA maturation by trans-encoded small RNA and host factor RNase III. Nature.—2011.—vol. 471.—Issue 7340.—p. 602.
Hsu PD, et al., DNA targeting specificity of RNA-guided Cas9 nucleases. Nat Biotechnol. Sep. 2013;31 (9):827-832.
Altschul et al., Basic local alignment search tool. J. Mol. Biol., 215, pp. 403-410 (1990).
Shen B, et al., Generation of gene-modified mice via Cas9/RNA-mediated gene targeting. Cell Res. May 2013;23(5):720-723.
Maxwell CS, et al., A detailed cell-free transcription-translation-based assay to decipher CRISPR protospacer-adjacent motifs. Meth-ods. Jul. 1, 2018 ;143:48-57.
Liu C et al., Delivery strategies of the CRISPR-Cas9 gene-editing system for therapeutic applications. J Control Release. Nov. 28, 2017;266:17-26.
Lino CA et al., Delivering CRISPR: a review of the challenges and approaches. Drug Deliv. Nov. 2018;25(1 ):1234-1257.
Lanford et al., Induction of nuclear transport with a synthetic peptide homologous to the SV40 T antigen transport signal. Cell, 1986, 46: 575-582.
Song M. The CRISPR/Cas9 system: Their delivery, in vivo and ex vivo applications and clinical development by startups. Biotechnol Prog. Jul. 2017;33(4):1035-1045 (Abstract).

* cited by examiner

A

Nucleotide PAM position

B

CAACATT    AAACATT    GAACATT    TAACATT 500
400
300
200
100

Fig. 13

DNA-CUTTING AGENT BASED ON CAS9 PROTEIN FROM THE BACTERIUM PASTEURELLA PNEUMOTROPICA

The content of the ASCII text file of the sequence listing named "P2364US00-SEQ-EN_PCTRU2020050137 28.05.2025" which is 20.1 kb in size, which was created on May 28, 2025 and electronically submitted herewith via EFS-Web is incorporated herein by reference.

FIELD OF INVENTION

The invention relates to biotechnology, specifically to novel Cas nuclease enzymes of CRISPR-Cas systems, which are used for cutting DNA and editing the genome of various organisms. This technique may be used in the future for gene therapy of hereditary human diseases, as well as for editing the genome of other organisms.

BACKGROUND OF THE INVENTION

Modification of a DNA sequence is one of the topical problems in today's biotechnology field. Editing and modifying the genomes of eukaryotic and prokaryotic organisms, as well as manipulating DNA in vitro, require targeted introduction of double-strand breaks in DNA sequences.

To solve this problem, the following techniques are currently used: artificial nuclease systems containing domains of the zinc finger type, TALEN systems, and bacterial CRISPR-Cas systems. The first two techniques require laborious optimization of a nuclease amino acid sequence for recognition of a specific DNA sequence. In contrast, when it comes to CRISPR-Cas systems, the structures that recognize a DNA target are not proteins, but short guide RNAs. Cutting of a particular DNA target does not require the synthesis of nuclease or its gene de novo but is made by way of using guide RNAs complementary to the target sequence. It makes CRISPR Cas systems convenient and efficient means for cutting various DNA sequences. The technique allows for simultaneous cutting of DNA at several regions using guide RNAs of different sequences. Such an approach is also used to simultaneously modify several genes in eukaryotic organisms.

By their nature, CRISPR-Cas systems are prokaryotic immune systems capable of highly specific introduction of breaks into a viral genetic material (Mojica F. J. M. et al. Intervening sequences of regularly spaced prokaryotic repeats derive from foreign genetic elements//Journal of molecular evolution.-2005.-Vol. 80.-Issue. 2.-pp. 174-182). The abbreviation CRISPR-Cas stands for "Clustered Regularly Interspaced Short Palindromic Repeats and CRISPR associated Genes" (Jansen R. et al. identification of genes that are associated with DMA repeats in prokaryotes//Molecular microbiology.-2002.-Vol. 43.-Issue. 8.-pp. 1565-1575). All CRISPR-Cas systems consist of CRISPR cassettes and genes encoding various Cas proteins (Jansen R. et al., Molecular microbiology.-2002.-Vol. 43.-Issue 6.-pp. 1565-1575). CRISPR cassettes consist of spacers, each having a unique nucleotide sequence, and repeated palindromic repeats (Jansen R. et al., Molecular microbiology.-2002.-Vol. 43.-Issue 6.-pp. 1565-1575). The transcription of CRISPR cassettes followed by processing thereof results in the formation of guide crRNAs, which together with Cas proteins form an effector complex (Brouns S. J. J. et ai. Small CRISPR RNAs guide antiviral defense in prokaryotes//Science.-2008.-Vol. 321.-Issue 5891.-pp. 960-964). Due to the complementary pairing between the crRNA and a target DNA site, which is called the protospacer, Cas nuclease recognizes a DNA target and highly specifically introduces a break therein.

CRISPR-Cas systems with a single effector protein are grouped into six different types (types I-VI), depending on Cas proteins that are included in the systems. In 2013, it was proposed for the first time to use the Type II CRISPR-Cas9 system for editing the genomic DNA of human cells (Cong L, et al., Multiplex genome engineering using CRISPR/Cas systems. Science. 2013 Feb. 15; 339(6121):819-23). The type II CRISPR-Cas9 system is characterized in its simple composition and mechanism of activity, i.e. its functioning requires the formation of an effector complex consisting only of one Cas9 protein and two short RNAs as follows: crRNA and tracer RNA (tracrRNA). The tracer RNA complementarily pairs with a crRNA region, which originates from a CRISPR repeat, to form a secondary structure necessary for the binding of guide RNAs to the Cas effector. Determining the sequence of guide RNAs is an important step in the characterization of previously unstudied Cas orthologues. The Cas9 effector protein is an RNA-dependent DNA endonuclease with two nuclease domains (HNH and RuvC) that introduce breaks into the complementary strands of target DNA, thus forming a double-strand DNA break (Deltcheva E. et al. CRISPR RNA maturation by trans-encoded small RNA and host factor RNase III//Nature.-2011.-Vol. 471.-Issue 7340.-p. 602).

Thus far, several CRISPR-Cas nucleases are known that are capable of targeted and specific introduction of double-strand breaks in DNA. The CRISPR-Cas9 technology is one of the most modern and rapidly developing techniques for introducing breaks in DNA of various organisms, ranging from bacterial strains to human cells, also offering in vitro application (Song M. The CRISPR/Cas9 system: Their delivery, in vivo and ex vivo applications and clinical development by startups. Biotechnol Prog. 2017 July; 33 (4): 1035-1045).

The effector ribonucleic complex consisting of Cas9 and a crRNA/tracrRNA duplex requires the presence of PAM (protospacer adjusted motif) on a DNA target for recognition and subsequent hydrolysis of DNA, in addition to crRNA spacer-protospacer complementarity. (Mojica F. J. M. et al. 2009). PAM is a strictly defined sequence of several nucleotides located in type II systems adjacent to or several nucleotides away from the 3' end of the protospacer on an off-target chain. In the absence of PAM, the hydrolysis of DNA bonds with the formation of a double-strand break does not take place. The need for the presence of a PAM sequence on a target increases recognition specificity but at the same time imposes restraints on the selection of target DNA regions for introducing a break. Thus, the presence of the desired PAM sequence flanking the DNA target from the 3'-end is a feature that limits the use of CRISPR-Cas systems at any DNA site.

Different CRISPR-Cas proteins use different, unique PAM sequences in the activity thereof. The use of CRISPR-Cas proteins with novel various PAM sequences is necessary to make it possible to modify any DNA region, both in vitro and in the genome of living organisms. Modification of eukaryotic genomes also requires the use of the small-sized nucleases to provide AAV-mediated delivery of CRISPR-Cas systems into cells.

Although a number of techniques for cutting DNA and modifying a genomic DNA sequence are known, there is still a need for novel effective means for modifying DNA in various organisms and at strictly specific sites of a DNA sequence.

SUMMARY OF THE INVENTION

The object of the present invention is to provide novel means for modifying a genomic DNA sequence of unicellular or multicellular organisms using CRISPR-Cas9 systems. Currently existing systems are of limited use due to a specific PAM sequence that must be present at the 3' end of the DNA region to be modified. Search for novel Cas9 enzymes with other PAM sequences will expand the range of available means for the formation of a double-strand break at desired, strictly specific sites in DNA molecules of various organisms. To solve this problem, the authors characterized the previously predicted for *Pasteurella pneumotropica* (*P. pneumotropica*) the type II CRISPR nuclease PpCas9, which can be used to introduce directed modifications into the genome of both the above and other organisms. The present invention is characterized in that it has the following essential features: (a) short PAM sequence that is different from other known PAM sequences; (b) relatively small size of the characterized PpCas9 protein, which is 1055 amino acid residues (a.a.r.).

Said problem is solved by using a protein comprising the amino acid sequence of SEQ ID NO: 1, or comprising an amino acid sequence that is at least 95% identical to the amino acid sequence of SEQ ID NO: 1 and differs from SEQ ID NO: 1 only in non-conserved amino acid residues, to form a double-strand break in a DNA molecule, located immediately before the nucleotide sequence 5'-NNNN(A/G)T-3' in said DNA molecule. In some embodiments of the invention, this use is characterized in that the double-strand break is formed in a DNA molecule at a temperature of 35° C. to 45° C.

Said problem is further solved by providing a method for modifying a genomic DNA sequence of a unicellular or multicellular organism, comprising the introduction, into at least one cell of said organism, of an effective amount of: a) either a protein comprising the amino acid sequence of SEQ ID NO: 1, or a nucleic acid encoding the protein comprising the amino acid sequence of SEQ ID NO: 1, and b) either a guide RNA comprising a sequence that forms a duplex with the nucleotide sequence of an organism's genomic DNA region, which is directly adjacent to the nucleotide sequence 5'-NNNN(A/G)T-3' and interacts with said protein following the formation of the duplex, or a DNA sequence encoding said guide RNA; wherein interaction of said protein with the guide RNA and the nucleotide sequence 5'-NNNN(A/G)T-3' results in the formation of a double-strand break in the genomic DNA sequence immediately adjacent to the sequence 5'-NNNN(A/G)T-3'. In some embodiments of the invention, the method is characterized in that it further comprises the introduction of an exogenous DNA sequence simultaneously with the guide RNA.

A mixture of crRNA and tracer RNA (tracrRNA), which can form a complex with a target DNA region and PpCas9 protein, may be used as a guide RNA. In preferred embodiments of the invention, a hybrid RNA constructed based on crRNA and tracer RNA may be used as a guide RNA. Methods for constructing a hybrid guide RNA are known to those skilled (Hsu P D, et al., DNA targeting specificity of RNA-guided Cas9 nucleases. Nat Biotechnol. 2013 September; 31 (9):827-32). One of the approaches for constructing a hybrid RNA has been disclosed in the Examples below.

The invention may be used both for in vitro cutting target DNA, and for modifying the genome of some living organism. The genome may be modified in a direct fashion, i.e. by cutting the genome at a corresponding site, as well as by inserting an exogenous DNA sequence via homologous repair.

Any region of double-strand or single-strand DNA from the genome of an organism other than that used for administration (or a composition of such regions among themselves and with other DNA fragments) may be used as an exogenous DNA sequence, wherein said region (or composition of regions) is intended to be integrated into the site of a double-strand break in target DNA, induced by PpCas9 nuclease. In some embodiments of the invention, a region of double-strand DNA from the genome of an organism used for the introduction of PpCas9 protein, further modified by mutations (substitution of nucleotides), as well as by insertions or deletions of one or more nucleotides, may be used as an exogenous DNA sequence.

The technical result of the present invention is to increase the versatility of the available CRISPR-Cas9 systems to enable the use of Cas9 nuclease for cutting genomic or plasmid DNA in a larger number of specific sites and specific conditions.

BRIEF DESCRIPTION OF DRAWINGS

FIG. 13. Alignment of amino acid sequences of PpCas9 and Cas9 proteins from *Staphylococcus aureus* using the NCBI BLASTp software (default parameters), showing SEQ ID NO: 1.

DETAILED DISCLOSURE OF THE INVENTION

Figure 1:
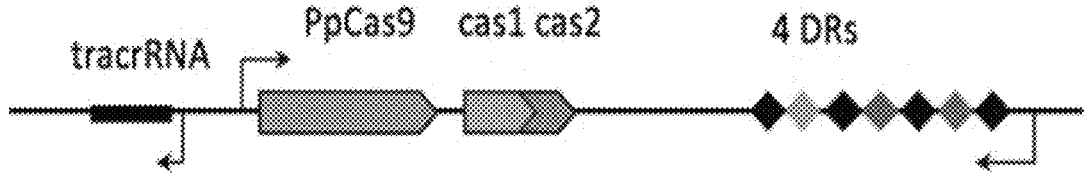
FIG. 1. Scheme of the locus of the CRISPR PpCas9 system. DR (direct repeat) is a regularly repeated region that is part of a CRISPR cassette.

As used in the description of the present invention, the terms "includes" and "including" shall be interpreted to mean "includes, among other things". Said terms are not intended to be interpreted as "consists only of". Unless defined separately, the technical and scientific terms in this application have typical meanings generally accepted in the scientific and technical literature.

As used herein, the term "percent homology of two sequences" is equivalent to the term "percent identity of two sequences". Sequence identity is determined based on a reference sequence. Algorithms for sequence analysis are known in the art, such as BLAST described in Altschul et al., J. Mol. Biol., 215, pp. 403-10 (1990). For the purposes of the present invention, to determine the level of identity and similarity between nucleotide sequences and amino acid sequences, the comparison of nucleotide and amino acid sequences may be used, which is performed by the BLAST software package provided by the National Center for Biotechnology Information (http://www.ncbi.nlm.nih.gov/blast) using gapped alignment with standard parameters. Percent identity of two sequences is determined by the number of positions of identical amino acids in these two sequences, taking into account the number of gaps and the length of each gap to be entered for optimal comparison of the two sequences by alignment. Percent identity is equal to the number of identical amino acids at given positions taking account of sequence alignment divided by the total number of positions and multiplied by 100.

The term "specifically hybridizes" refers to the association between two single-strand nucleic acid molecules or sufficiently complementary sequences, which permits such hybridization under pre-determined conditions typically used in the art.

The phrase "a double-strand break located immediately before the nucleotide PAM sequence" means that a double-strand break in a target DNA sequence will be made at a distance of 0 to 25 nucleotides before the nucleotide PAM sequence.

An exogenous DNA sequence introduced simultaneously with a guide RNA is intended to refer to a DNA sequence prepared specifically for the specific modification of a double-strand target DNA at the site of break determined by the specificity of the guide RNA. Such a modification may be, for example, an insertion or deletion of certain nucleotides at the site of a break in target DNA. The exogenous DNA may be either a DNA region from a different organism or a DNA region from the same organism as that of target DNA.

A protein comprising a specific amino acid sequence is intended to refer to a protein having an amino acid sequence composed of said amino acid sequence and possibly other sequences linked by peptide bonds to said amino acid sequence. An example of other sequences may be a nuclear localization signal (NLS), or other sequences that provide increased functionality for said amino acid sequence.

An exogenous DNA sequence introduced simultaneously with a guide RNA is intended to refer to a DNA sequence prepared specifically for the specific modification of a double-strand target DNA at the site of break determined by the specificity of the guide RNA. Such a modification may be, for example, an insertion or deletion of certain nucleotides at the site of a break in target DNA. The exogenous DNA may be either a DNA region from a different organism or a DNA region from the same organism as that of target DNA.

An effective amount of protein and RNA introduced into a cell is intended to refer to such an amount of protein and RNA that, when introduced into said cell, will be able to form a functional complex, i.e. a complex that will specifically bind to target DNA and produce therein a double-strand break at the site determined by the guide RNA and PAM sequence on DNA. The efficiency of this process may be assessed by analyzing target DNA isolated from said cell using conventional techniques known to those skilled.

A protein and RNA may be delivered to a cell by various techniques. For example, a protein may be delivered as a DNA plasmid that encodes a gene of this protein, as an mRNA for translation of this protein in cell cytoplasm, or as a ribonucleoprotein complex that includes this protein and a guide RNA. The delivery may be performed by various techniques known to those skilled.

The nucleic acid encoding system's components may be introduced into a cell directly or indirectly as follows: by way of transfection or transformation of cells by methods known to those skilled, by way of the use of a recombinant virus, by way of manipulations on the cell, such as DNA microinjection, etc.

A ribonucleic complex consisting of a nuclease and guide RNAs and exogenous DNA (if necessary) may be delivered by way of transfecting the complexes into a cell or by way of mechanically introducing the complex into a cell, for example, by way of microinjection.

A nucleic acid molecule encoding the protein to be introduced into a cell may be integrated into the chromosome or may be an extrachromosomally replicating DNA. In some embodiments, to ensure effective expression of the protein gene with DNA introduced into a cell, it is necessary to modify the sequence of said DNA in accordance with the cell type in order to optimize the codons for expression, which is due to unequal frequencies of occurrence of synonymous codons in the coding regions of the genome of various organisms. Codon optimization is necessary to increase expression in animal, plant, fungal, or microorganism cells.

For a protein that has a sequence that is at least 95% identical to the amino acid sequence of SEQ ID NO: 1 to function in a eukaryotic cell, it is necessary for this protein to end up in the nucleus of this cell. Therefore, in some embodiments of the invention, a protein having a sequence that is at least 95% identical to the amino acid sequence of SEQ ID NO: 1 and which is further modified at one or both ends by the addition of one or more nuclear localization signals is used to form double-strand breaks in target DNA. For example, a nuclear localization signal from the SV40 virus may be used. To provide efficient delivery to the nucleus, the nuclear localization signal may be separated from the main protein sequence by a spacer sequence, for example, described in Shen B, et al. "Generation of gene-modified mice via Cas9/RNA-mediated gene targeting", Cell Res. 2013 May; 23(5): 720-3. Further, in other embodiments, a different nuclear localization signal or an alternative method for delivering said protein into the cell nucleus may be used.

The present invention encompasses the use of a protein from the *P. pneumotropica* organism, which is homologous to the previously characterized Cas9 proteins, to introduce double-strand breaks into DNA molecules at strictly specified positions. The use of CRISPR nucleases to introduce targeted modifications to the genome has a number of advantages. First, the specificity of the system's activity is determined by a crRNA sequence, which allows for the use of one type of nuclease for all target loci. Secondly, the technique enables the delivery of several guide RNAs complementary to different gene targets into a cell at once, thereby making it possible to simultaneously modify several genes at once.

PpCas9 is a Cas nuclease found in *Pasteurella pneumo-tropica* ATCC 35149, a rodent pathogen that lives in the lungs of the animals. The *Pasteurella pneumotropica* (*P. pneumotropica*) CRISPR Cas9 system (hereinafter referred to as CRISPR PpCas9) belongs to type II-C CRISPR Cas systems and consists of a CRISPR cassette carrying four direct repeats (DR) with the sequence 5'ATTATAGCACTGCGAAATGAAAAAGGGAGCTA-CAAC3' (corresponding to SEQ ID NO: 3), interspaced by the sequences of unique spacers. None of the spacers of the system coincides in sequence with the currently known bacteriophages or plasmids, which fact makes it impossible to determine the PpCas9 PAM of interest by bioinformatic analysis. To the CRISPR cassette there are adjacent the gene for the effector Cas9 protein PpCas9, as well as the genes for the Cas1 and Cas2 proteins involved in adaptation and integration of new spacers. Nearby the Cas genes, a sequence was found partially complementary to direct repeats and folding into a characteristic secondary structure, which is contemplated to be the tracer RNA (tracrRNA) (FIG. 1)

Knowledge of the characteristic architecture of the RNA-Cas protein complex of type II-C systems made it possible to predict the direction of transcription of the CRISPR cassette: pre-crRNA is transcribed in the opposite direction to the Cas genes (FIG. 1)

Thus, the analysis of the sequence of the PpCas9 locus made it possible to predict the sequences of tracer and guide RNAs (Table 1).

TABLE 1

Sequences of guide RNAs of the CRISPR PpCas9
system, which were determined by bioinformatics
methods. Bold indicates the sequence of
direct repeat, DR.

| Name | Sequence |
| --- | --- |
| PpCas9 trRNA | 5'GCGAAATGAAAAACGUUGUUACAAUAAGAGAUGAAUUGCU CGCAAAGCTCUGCCUCUUGAAAUUUCGGUUUCAAGAGGCAUC UUUUU-3' (SEQ ID NO: 4) |
| PpCas9 crRNA | 5'-xxxxxxxxxxxxxxxxxxxxxxGUUGUAGCUCCCUUUUCAU UUCGC-3' (SEQ ID NO: 5) |

To verify the activity of PpCas9 nuclease and determine the PpCas9 PAM of interest, we conducted experiments on recreating the DNA cutting reaction in vitro. To determine the PAM sequence of the PpCas9 protein, in vitro cutting of double-strand PAM libraries was employed. To this end, it was necessary to obtain all the components of the PpCas9 effector complex as follows: guide RNAs and a nuclease in a recombinant form. Determination of the guide RNA sequence made it possible to synthesize crRNA and tracrRNA molecules in vitro. The synthesis was carried out using the NEB HiScribe T7 RNA synthesis kit. The double-strand DNA libraries were 374 base pair (bp) fragments comprising a protospacer sequence flanked by randomized seven nucleotides (5'-NNNNNNN-3') from the 3' end:

(SEQ ID NO: 6)
5'-cccggggtaccacggagagatggtggaaatcatctttctcgtgggca tccttgatggccacctcgtcggaagtgcccacgaggatgacagcaatgcc aatgctgggggggctcttctgagaacgagctctgctgcctgacacggcca ggacggccaacaccaaccagaacttgggagaacagcactccgctctgggc

8

-continued ttcatcttcaactcgtcgactccctgcaaacacaaagaaagagcatgtta aaataggatctacatcacgtaacctgtcttagaagaggctagatactgca attcaaggaccttatctcctttcattgagcacNNNNNNNNaactccatcta ccagcctactctcttatctctggtatt-3'

To cut this target, guide RNAs of the following sequence were used:

tracrRNA:
(SEQ ID NO: 7)
5'GCGAAATGAAAAACGUUGUUACAAUAAGAGAUGAAUUUCUCGCAAAGC

TCUGCCUCUUGAAAUUUCGGUUUCAAGAGGCAUCUUUUU
and crRNA:
(SEQ ID NO: 8)
5' uaucuccuuucauugagcacGUUGUAGCUCCCUUUUUCAUUUCGC.

Bold indicates the crRNA sequence that is complementary to the protospacer (target DNA sequence).

To produce a recombinant PpCas9 protein, the gene thereof was cloned into the plasmid pET21a. DNA synthesized by Integrated DNA Technologies (IDT) was used as the DNA encoding the gene. The sequence was codon-optimized to exclude rare codons found in the *P. pneumotropica* genome. *E. coli* Rosetta cells were transformed with the resulting plasmid pET21 a-6×His-PpCas9.

500 μl of overnight culture was diluted in 500 ml of LB medium, and the cells were grown at 37° C. until an optical density of 0.6 Ru was obtained. The synthesis of the target protein was induced by adding IPTG to a concentration of 1 mM, the cells were then incubated at 20° C. for 6 hours. Then, the cells were centrifuged at 5,000 g for 30 minutes, the resulting cellular precipitates were frozen at −20° C.

The precipitates were thawed on ice for 30 minutes, resuspended in 15 ml of lysis buffer (Tris-HCl 50 mM pH 8, 500 mM NaCl, b-mercaptoethanol 1 mM, imidazole 10 mM) supplemented with 15 mg of lysozyme and re-incubated on ice for 30 minutes. The cells were then disrupted by sonication for 30 minutes and centrifuged for 40 minutes at 16,000 g. The resulting supernatant was passed through a 0.2 μm filter and applied onto a HisTrap HP 1 mL column (GE Healthcare) at 1 ml/min.

Chromatography was performed using the AKTA FPLC chromatograph (GE Healthcare) at 1 ml/min. The column with the applied protein was washed with 20 ml of lysis buffer supplemented with 30 mM imidazole, after which the protein was washed off with lysis buffer supplemented with 300 mM imidazole.

Then, the protein fraction obtained in the course of affinity chromatography was passed through a Superdex 200 10/300 GL gel filtration column (24 ml) equilibrated with the following buffer: Tris-HCl 50 mM pH 8, 500 mM NaCl, 1 mM DTT. Using an Amicon concentrator (with a 30 kDa filter), fractions corresponding to the monomeric form of the PpCas9 protein were concentrated to 3 mg/ml, after which the purified protein was stored at −80° C. in a buffer containing 10% glycerol.

Figure 2:
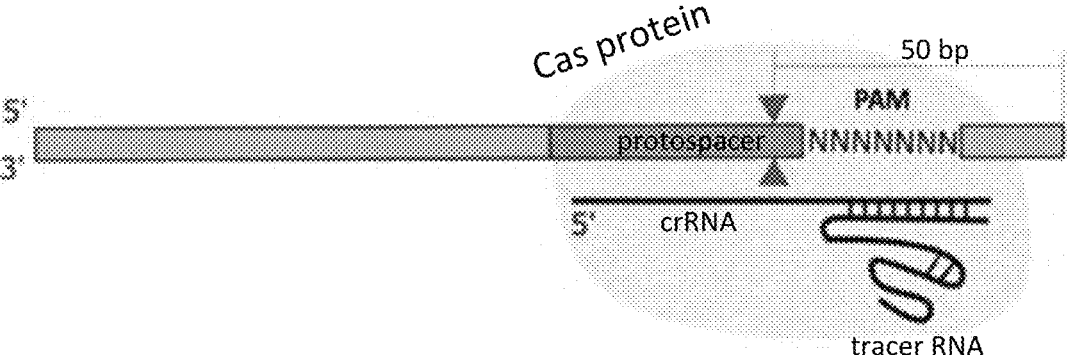
FIG. 2. In vitro PAM screening. Scheme of the experiment.

The in vitro reaction of cutting the linear PAM libraries was carried out in a volume of 20 μl under the following conditions. The reaction mixture consisted of: 1× CutSmart buffer (NEB), 5 mM DTT, 100 nM PAM library, 2 μM trRNA/crRNA, 400 nM PpCas9 protein. As a control, samples containing no RNA were prepared in a similar way. The samples were incubated at different temperatures and analyzed by gel electrophoresis in 2% agarose gel. In the case of correct recognition and specific cutting of DNA by PpCas9 protein, two DNA fragments of about 326 and 48 base pairs should be generated (see FIG. 2).

Figure 3:
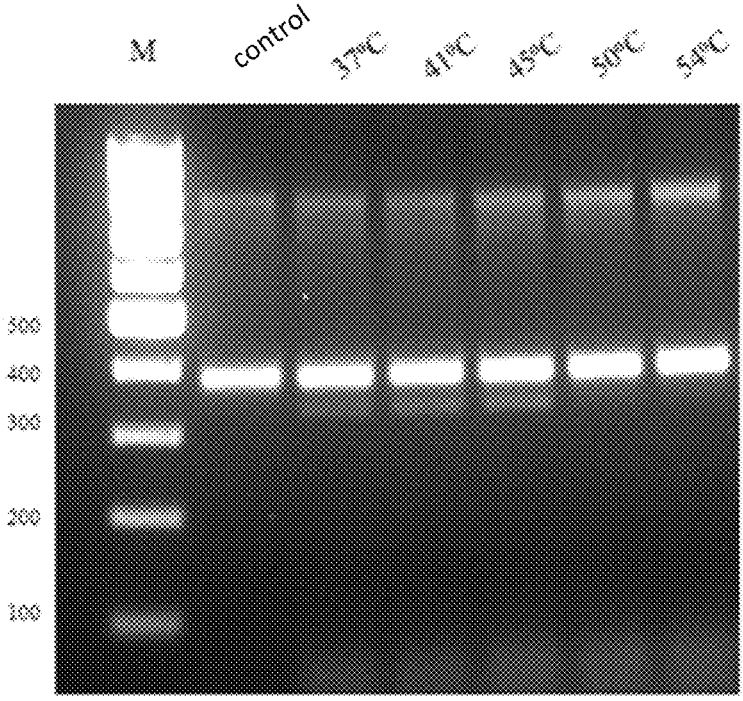
FIG. 3. PpCas9 nuclease cutting of 7N library fragments at different reaction temperatures.

The experiment results showed that PpCas9 has nuclease activity and cuts a portion of the PAM library fragments. The temperature gradient (FIG. 3) showed that the protein is active in the temperature range of 35-45 C. The study then used a temperature of 42° C. as a working temperature.

Figure 4:
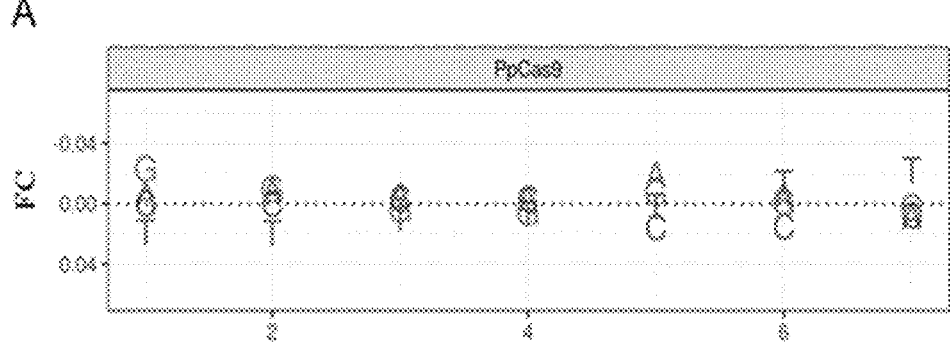
FIG. 4. (A) Analysis of the results of in vitro screening of PpCas9 nuclease using the calculation of the proportion change logarithm for each specific nucleotide in each PAM (FC) position. (B) PAM Logo of PpCas9 nuclease. The occurrence of Adenine, Cytosine, Thymine, and Guanine is indicated for each position. The height of the letters corresponds to the occurrence of nucleotide at a given position of PAM sequence.

The library cutting reaction was repeated under the selected conditions. The reaction products were applied onto 1.5% agarose gel and subjected to electrophoresis. Uncut DNA fragments with a length of 374 bp were extracted from the gel and prepared for high-throughput sequencing using the NEB NextUltra II kit. The samples were sequenced on the Illumina platform, and then the analysis of the sequences was carried out using bioformatical methods: we determined the difference in occurrence of nucleotides at individual positions of PAM (NNNNNNN) as compared to the control sample using the approach described in (Maxwell C S, et al., A detailed cell-free transcription-translation-based assay to decipher CRISPR protospacer-adjacent motifs. Methods. 2018 Jul. 1; 143:48-57). Furthermore, PAM logo was built to analyze the results (FIG. 4).

Both approaches to data analysis (FIG. 4) indicate the significane of PAM positions 5, 6 and 7. Thus, in vitro analysis allowed to establish the putative PAM sequence for PpCas9 as follows: NNNNATT. However, this sequence is only putative in view of inaccurate results obtained by screening approaches to determine PAM.

In this regard, the significance of individual PAM sequence positions was verified for more precise determination of the sequence. To this end, we performed in vitro reactions of cutting of DNA fragments containing a DNA target 5'-atctcctttcattgagcac-3' flanked by PAM sequence CAACATT (or derivatives thereof):

(SEQ ID NO: 9)
5'-cccgggGtaccacggagagatggtggaaatcatctttctcgtgggca tccttgatggccacctcgtcggaagtgcccacgaggatgacagcaatgcc aatgctggggggctcttctgagaacgagctctgctgcctgacacggcca ggacggccaacaccaaccagaacttgggagaacagcactccgctctgggc ttcatcttcaactcgtcgactccctgcaaacacaaagaaagagcatgtta aaataggatctacatcacgtaacctgtcttagaagaggctagatactgca attcaaggaccttatctcctttcattgagcacCAACATTaactccatcta ccagcctactctcttatctctggtatt-3'

All DNA cutting reactions were performed under the following conditions:
   IxCutSmart buffer
   400 nM PpCas9
   20 nM DNA
   2 μM crRNA
   2 μM tracrRNA
   Incubation time was 30 minutes, reaction temperature was 42° C.

Figures 5, 6:
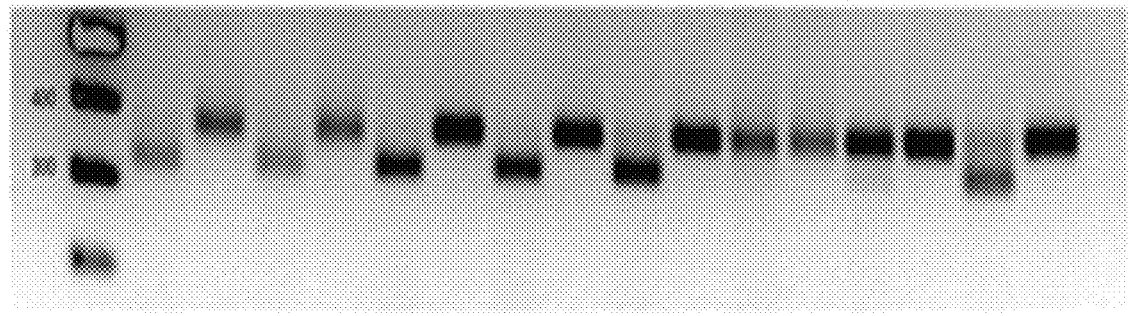
FIG. 5. Verification of the effect of single-nucleotide substitutions at PAM position 1 on the efficiency of cutting the DNA target by PpCas9 nuclease.
FIG. 6. Verification of the significance of nucleotide positions in the PpCas9 PAM sequence.

The substitution of PAM position 1 with all four possible nucleotide variants did not affect the efficiency of protein activity (FIG. 5).

Figure 7:
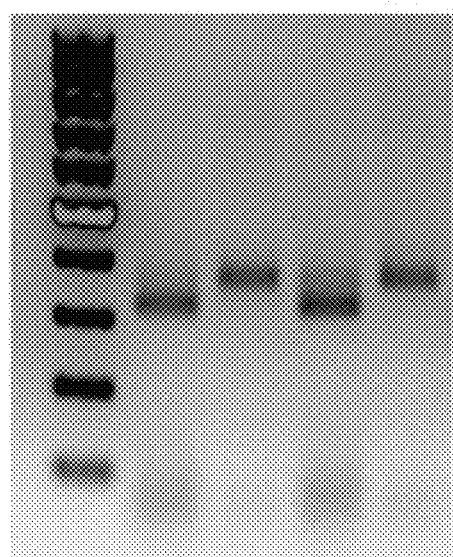
FIG. 7. Verification of the effect of A to G substitution at PAM position 6 on the efficiency of cutting of the DNA target by PpCas9 nuclease.

The predicted significance of positions 5 and 6 was confirmed experimentally by single nucleotide substitutions (purine with pyrimidine and vice versa) in each of the PAM positions. When the substitutions took place at positions 5 and 6, the protein practically stopped its activity. When the substitution took place at position 7, the efficiency of PpCas9 activity decreased twice, which fact reflects the reduced requirements for the nucleotide at this position (FIG. 6). Thus, according to the results of in vitro PAM screening of PpCas9 nuclease, the most probable nucleotides at PAM position 5 are adenine or guanine, which fact was confirmed experimentally (FIG. 7). A to G substitution did not reduce the efficiency of cutting of the fragment.

Figure 8:
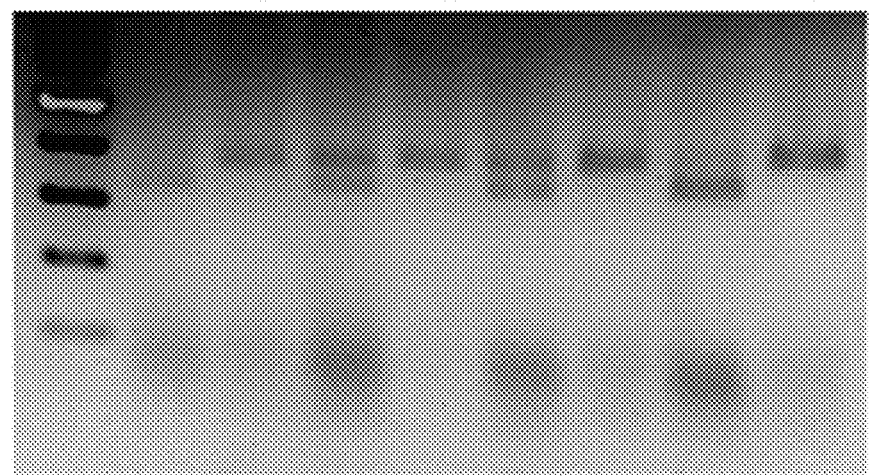
FIG. 8. Verification of the effect of single-nucleotide substitutions at PAM position 7 on the efficiency of cutting the DNA target by PpCas9 nuclease.

According to the results of in vitro screening, fragments with "T" or with "S" at position 7 should be recognized more efficiently. Additional experiments were conducted to definitively verify the significance of nucleotides at this position. The results of in vitro tests showed that substitution of the nucleotide "T" at position 7 with A or G reduced the cutting efficiency by 40-50% (FIG. 8). Thus, PAM position 7 is less conserved as compared to positions 5 and 6: purines at position 7 only reduce recognition efficiency but do not prevent PpCas9 protein to introduce double-strand breaks into DNA.

The results of the study were as follows: PAM recognized by PpCas9 nuclease corresponds to the following formula 5'-NNNN(A/G)T-3'. The sequences NNNNRTY (NNNN (A/G)-T-(T/C)) are recognized more efficiently as compared to NNNNRTR (NNNN-(A/G)-T-(A/G)).

The following exemplary embodiments of the method are given for the purpose of disclosing the characteristics of the present invention and should not be construed as limiting in any way the scope of the invention.

Example 1. Testing the Activity ofPpCas9 Protein in the Cutting of Various DNA Targets In order to check the ability ofPpCas9 to recognize various DNA sequences flanked by the sequence 5'-NNNN (A/G)T-3', experiments were conducted on in vitro cutting of DNA targets from a human grin2b gene sequence (see Table 2).

TABLE 2

DNA targets from the human grin2b gene.

| sequence | PAM | | | | | | |
|---|---|---|---|---|---|---|---|
| TATCTCCTTCATTGAGCAC (SEQ ID NO: 10) | C | A | A | A | C | C | C |
| CAGCTGAAGTAATGTTAGAG (SEQ ID NO: 11) | G | C | A | C | A | T | T |
| AATAAGAAAAACATTATTAT (SEQ ID NO: 12) | C | A | C | C | A | T | T |
| GGGGCTATAAGTACACAAGC (SEQ ID NO: 13) | C | C | T | G | C | A | T |
| CGTTCTCAGAAGAGCCCCCC (SEQ ID NO: 14) | C | A | G | C | A | T | T |
| CCCACGAGAAAGATGATTTC (SEQ ID NO: 15) | C | A | C | C | A | T | C |

A PCR fragment of the grin2b gene carrying recognition sites (Table 2) presumably recognizable by PpCas9 in accordance with PAM consensus sequence 5'-NNNN(A/G)T-3' was used as a target in the cutting reaction. crRNAs directing PpCas9 to these sites were synthesized to recognize these sequences.

Figure 9:
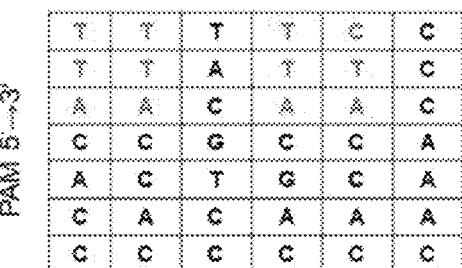
FIG. 9. Cutting of various DNA sites using the PpCas9 protein. Lanes 1 and 2 are positive controls.
Figure 9:
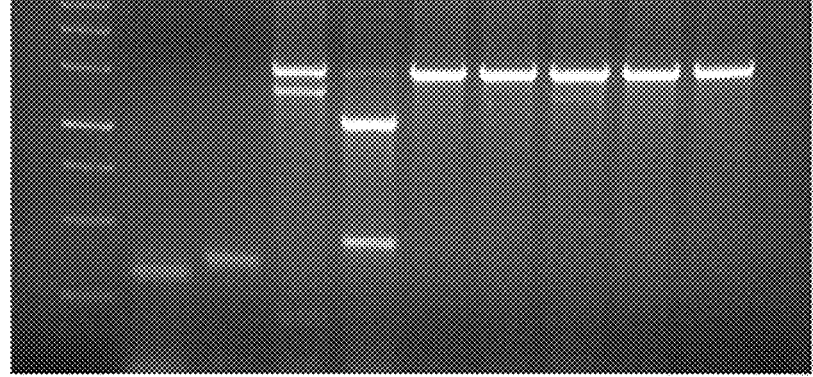

The cutting reactions were performed under conditions selected for PpCas9; the result is shown in FIG. 9. FIG. 9 shows that the PpCas9 enzyme successfully cut three of the four targets with suitable PAM.

The target on lane 6 had PAM sequence CAGCATT, which, according to the predictions based on the results of depletion analysis, should be efficiently recognized by the protein. However, the recognition of this fragment did not take place in this experiment.

Figure 10:
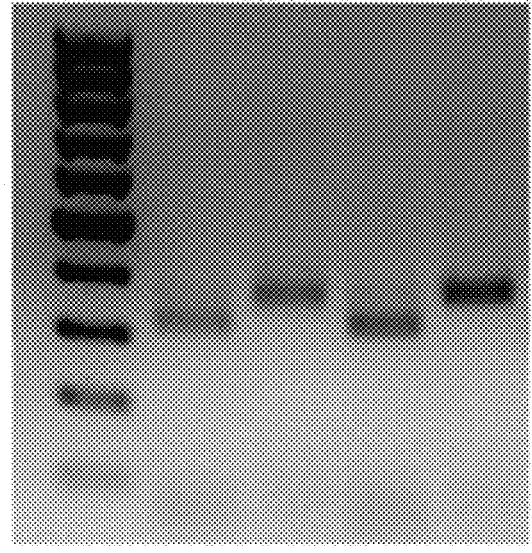
FIG. 10. Verification of recognition of the PAM sequence CAGCATT by PpCas9 nuclease. Lanes 1 and 2 are positive controls.

Therefore, the PAM CAGCATT was additionally verified on another protospacer target restricted to the same PAM (FIG. 10). In this case, the PAM was effectively recognized, which resulted in the cutting of DNA. Thus, the protein has some further preferences for the DNA target sequence. The preferences are possibly related to the secondary structure of DNA.

Thus, the studies showed the presence of nuclease activity in PpCas9, and also allowed to determine its PAM sequence and to verify the sequences of guide RNAs.

Figure 11:
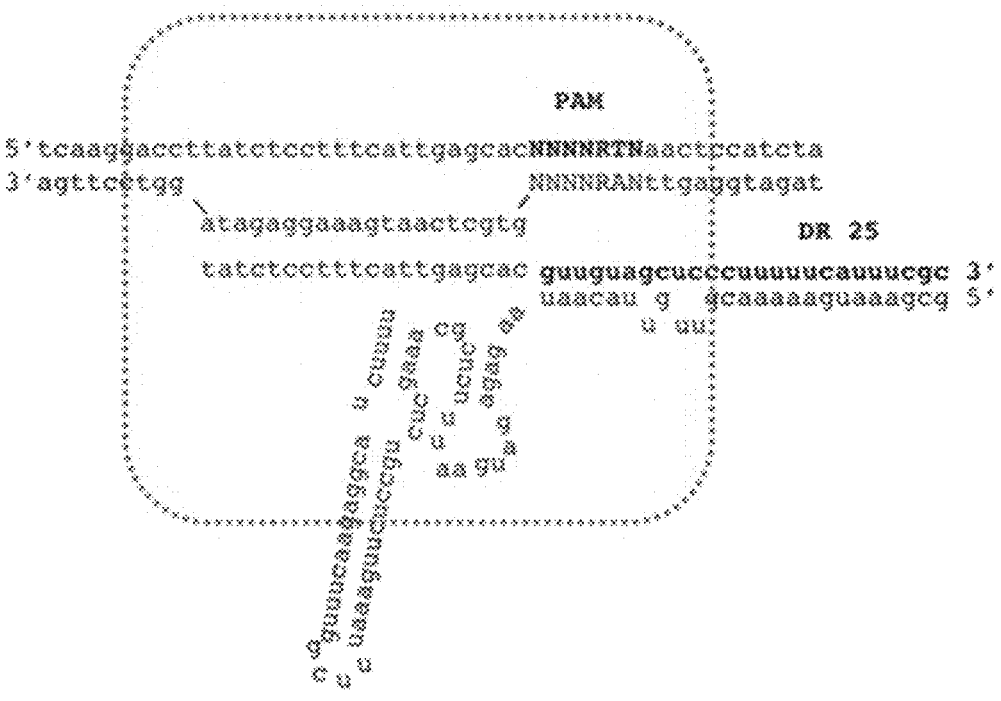
FIG. 11. Diagram of the DNA cutting tool PpCas9, showing SEQ ID NOs: 5, 6, 10, 25, 26 and 27.

The PpCas9 ribonucleoprotein complex specifically introduces breaks in targets restricted to the PAM 5' NNNN(A/G)T 3' from the 5' end of the protospacer. The scheme of the PpCas9/RNA complex is shown in FIG. 11.

Figure 12:
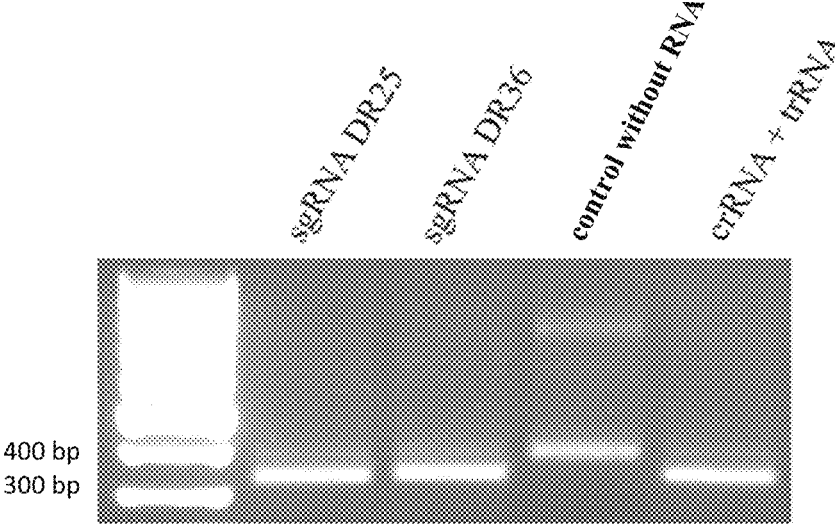
FIG. 12. Experiment on cutting of a DNA target. Hybrid guide RNAs of different lengths were used.

Example 2. Use of Hybrid Guide RNA for Cutting a DNA Target sgRNA is a form of guide RNAs, which is fused tracrRNA (tracer RNA) and crRNA. To select the optimal sgRNA, we constructed three variants of this sequence, which differed in the length of the tracrRNA-crRNA duplex. RNAs was synthesized in vitro and experiments involving them were conducted on cutting the DNA target (FIG. 12).

The following RNA sequences were used as hybrid RNAs:

```
1 - sgRNAI 25DR:
                                      (SEQ ID NO: 16)
UAUCUCCUUUCAUUGAGCACGUUGUAGCUCCCUUUUUCAUUUCGCGAAAG

CGAAAUGAAAAACGUUGUUACAAUAAGAGAUGAAUUUCUCGCAAAGCTCT

GCCUCUUGAAAUUUCGGUUUCAAGAGGCAUCUUUUU

2 - sgRNA2 36DR
                                      (SEQ ID NO: 17)
UAUCUCCUUUCAUUGAGCACGUUGUAGCUCCCUUUUUUCAUUUCGCAGUG

CUAUAAUGAAAAUUAUAGCACUGCGAAAUGAAAAACGUUGUUACAAUAAG

AGAUGAAUUUCUCGCAAAGCUCUGCCUCUUGAAAUUUCGGUUUCAAGAGG

CAUCUUUUU
```

Bold indicates a 20-nucleotide sequence that provides pairing with the target DNA (variable portion of sgRNA). Furthermore, the experiment used a control sample without RNA and a positive control, which is the cutting of the target using crRNA+trRNA.

A sequence containing the recognition site 5' tatctccttt-cattgagcac 3' (SEQ ID NO: 18) with the corresponding consensus sequence PAMCAACATT was used as a DNA target:

```
                                      (SEQ ID NO: 19)
5'-cccggggtaccacggagagatggtggaaatcatctttctcgtgggca tccttgatggccacctcgtcggaagtgcccacgaggatgacagcaatgcc aatgctgggggggctcttctgagaacgagctctgctgcctgacacggcca
```

```
                    -continued
ggacggccaacaccaaccagaacttgggagaacagcactccgctctgggc ttcatcttcaactcgtcgactccctgcaaacacaaagaaagagcatgtta aaataggatctacatcacgtaacctgtcttagaagaggctagatactgca attcaaggaccttatctcctttcattgagcacCAACATTcaactccatct accagcctactctcttatctctggtatt-3
```

Bold indicates the recognition site, capital letters stand for PAM.

The reaction was performed under the following conditions: concentration of DNA sequence containing PAM (CAACATT) was 20 nM, protein concentration was 400 nM, RNA concentration was 2 µM; incubation time was 30 minutes, incubation temperature was 37° C.

The selected sgRNA1 and sgRNA2 were found to be as efficient as the native tracrRNA and crRNA sequences: cutting took place in more than 80% of the DNA targets (FIG. 12).

These hybrid RNA variants may be used to cut any other target DNA after modifying the sequence that directly pairs with the DNA target.

Example 3. Cas9 Proteins from Closely Related Organisms Belonging to P. pneumotropica To date, no CRISPR-Cas9 enzymes have been characterized in P. pneumotropica. The Cas9 protein from Staphylococcus aureus, which is comparable in size, is identical to PpCas9 by 28% ((FIG. 13, the degree of identity was calculated by BLASTp software, default parameters). A similar degree of identity is present in other known Cas9 proteins (not shown).

Thus, PpCas9 protein differs significantly in its amino acid sequence from other Cas9 proteins studied to date.

Figure 13:
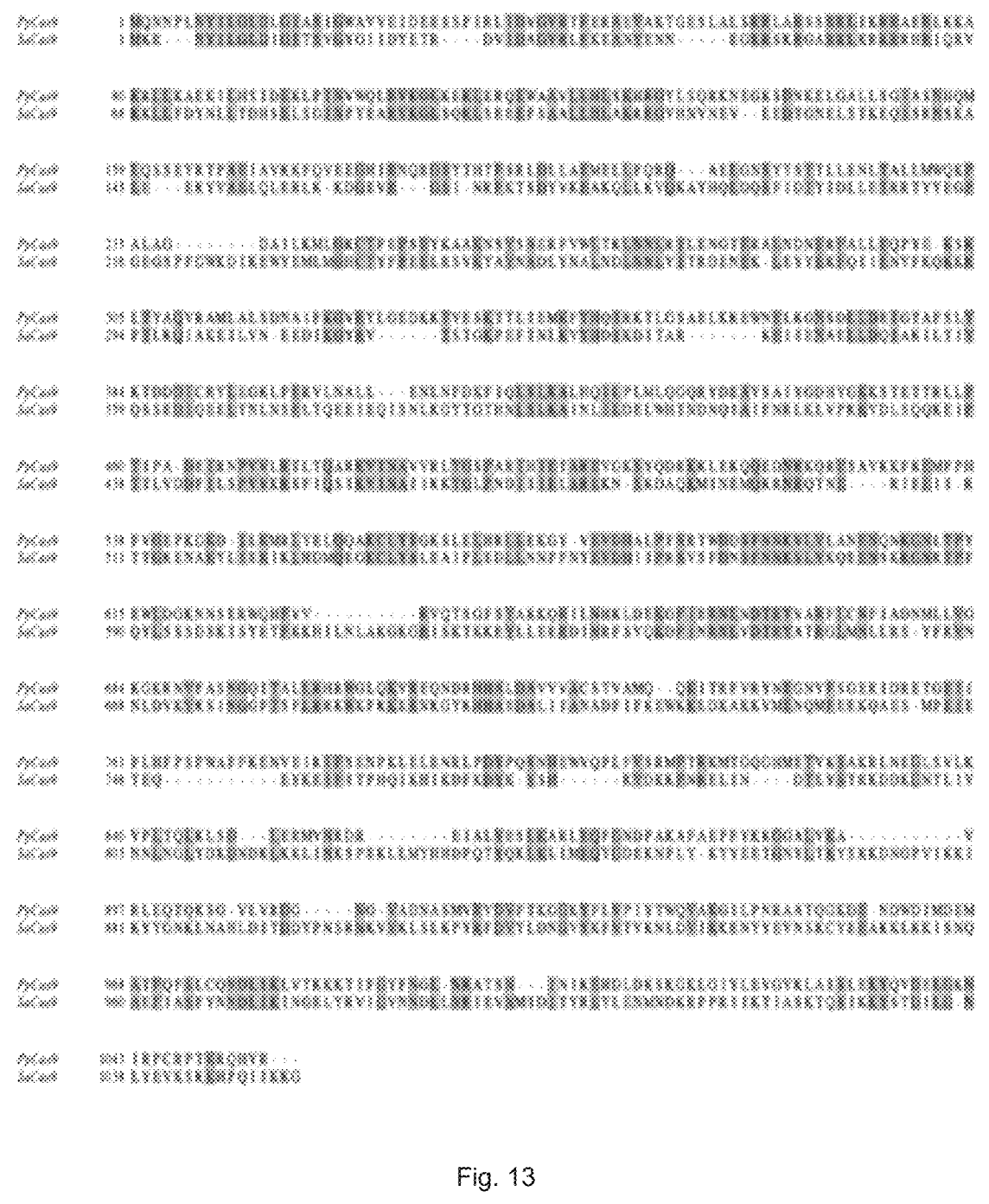

Those skilled in the art of genetic engineering will appreciate that PpCas9 protein sequence variant obtained and characterized by the Applicant in the present description may be modified without changing the function of the protein itself (for example, by directed mutagenesis of amino acid residues that do not directly influence the functional activity (Sambrook et al., Molecular Cloning: A Laboratory Manual, (1989), CSH Press, pp. 15.3-15.108)). In particular, those skilled will recognize that non-conserved amino acid residues may be modified, without affecting the residues that are responsible for protein functionality (determining protein function or structure). Examples of such modifications include the substitutions of non-conserved amino acid residues with homologous ones. Some of the regions containing non-conserved amino acid residues are shown in FIG. 13. In some embodiments of the invention, it is possible to use a protein comprising an amino acid sequence that is at least 95% identical to the amino acid sequence of SEQ ID NO: 1 and differs from SEQ ID NO: 1 only in non-conserved amino acid residues, to form, in DNA molecule, a double-strand break located immediately before the nucleotide sequence 5'-NNNN(A/G)T-3' in said DNA molecule. Homologous proteins may be obtained by mutagenesis (for example, site-directed or PCR-mediated mutagenesis) of corresponding nucleic acid molecules, followed by testing the encoded modified Cas9 protein for the preservation of its functions in accordance with the functional analyses described herein.

Example 4. The PpCas9 system described in the present invention, in combination with guide RNAs, may be used to modify the genomic DNA sequence of a multicellular organism, including a eukaryotic organism. For introducing the PpCas9 system in the complex with guide RNAs into the cells of this organism (into all cells or into a portion of cells), various approaches known to those skilled may be applied. For example, methods for delivering CRISPR-Cas9 systems to the cells of organisms have been disclosed in the sources (Liu C et al., Delivery strategies of the CRISPR-Cas9 gene-editing system for therapeutic applications. J Control Release. 2017 Nov. 28; 266:17-26; Lino C A et al., Delivering CRISPR: a review of the challenges and approaches. Drug Deliv. 2018 November; 25(1):1234-1257), and in the sources further disclosed within these sources.

For effective expression of PpCas9 nuclease in eukaryotic cells, it will be desirable to optimize codons for the amino acid sequence of PpCas9 protein by methods known to those skilled (for example, IDT codon optimization tool).

For the effective activity of PpCas9 nuclease in eukaryotic cells, it is necessary to import the protein into the nucleus of a eukaryotic cell. This may be done by way of using a nuclear localization signal from SV40 T-antigen (Lanford et al., Cell, 1986, 46:575-582) linked to PpCas9 sequence via a spacer sequence described in Shen B, et al. "Generation of gene-modified mice via Cas9/RNA-mediated gene targeting", Cell Res. 2013 May; 23(5):720-3 or without the spacer sequence. Thus, the complete amino acid sequence of nuclease to be transported inside the nucleus of a eukaryotic cell will be the following sequence: (SEQ ID NO: 20) MAPKKKRKVGIHGVPAA-PpCas9-KRPAATKK-AGQAKKKK (SEQ ID NO: 21) (hereinafter referred to as PpCas9 NLS). A protein with the above amino acid sequence may be delivered using at least two approaches.

Gene delivery is accomplished by creating a plasmid bearing the PpCas9 NLS gene under control of a promoter (for example, the CMV promoter) and a sequence encoding guide RNAs under control of the U6 promoter. As DNA targets, DNA sequences flanked by 5'-NNNN (G/A) T-3' are used, for example, those of the human grin2b gene:

5'-CAGCTGAAGTAATGTTAGAG-3' (SEQ ID NO: 22)

Thus, the sgRNA expression cassette looks as follows:

(SEQ ID NO: 23)
gagggcctatttcccatgattccttcatatttgcatatacgatacaaggc tgttagagagataattggaattaatttgactgtaaacacaaagatattag tacaaaatacgtgacgtagaaagtaataatttcttgggtagtttgcagtt ttaaaattatgttttaaaatggactatcatatgcttaccgtaacttgaaa gtatttcgatttcttggctttatatatcttgtggaaaggacgaaacaccg (SEQ ID NO: 24)
CAGCTGAAGTAATGTTAGAGGTTGTAGCTCCCTTTTTCATTTCGCGAAAG

CGAAATGAAAAACGTTGTTACAATAAGAGATGAATTTCTCGCAAAGCTCT

GCCTCTTGAAATTTCGGTTTCAAGAGGCATCTTTTT

Bold indicates the U6 promoter sequence, followed by a sequence required to recognize the DNA target, and further followed by the sequence forming the sgRNA structure, which is highlighted in red.

Plasmid DNA is purified and transfected into human HEK293 cells using Lipofectamine 2000 reagent (Thermo Fisher Scientific). The cells are incubated for 72 hours, then genomic DNA is extracted therefrom using genomic DNA purification columns (Thermo Fisher Scientific). The target DNA site is analyzed by sequencing on the Illumina platform in order to determine the number of insertions/deletions in DNA that take place in the target site due to a directed double-strand break followed by repair thereof.

Amplification of the target fragments is performed using primers flanking the presumptive site of break introduction.

After amplification, samples are prepared according to the Ultra II DNA Library Prep Kit for Illumina (NEB) reagent sample preparation protocol for high-throughput sequencing. Sequencing is then performed on the Illumina platform, 300 cycles, direct reading. The sequencing results are analyzed by bioinformatic methods. An insertion or deletion of several nucleotides in the target DNA sequence is taken as a cut detection.

Delivery as a ribonucleic complex is carried out by incubating recombinant PpCas9 NLS with guide RNAs in the CutSmart buffer (NEB). The recombinant protein is produced from bacterial producer cells by purifying the former by affinity chromatography (NINTA, Qiagen) with size exclusion (Superdex 200).

The protein is mixed with RNAs in a ratio of 1:2 (PpCas9 NLS:sgRNA), the mixture is incubated for 10 minutes at room temperature, and then transfected into the cells.

Next, the DNA extracted therefrom is analyzed for insertions/deletions at the target DNA site (as described above).

The PpCas9 nuclease disclosed in the present invention from the bacterium *Pasteurella pneumotropica* has a number of advantages over the previously disclosed Cas9 proteins.

PpCas9 has a short, two-letter PAM, distinct from other known Cas nucleases, that is required for the system to function. The invention has shown that the presence of a short PAM (RT) located 4 nucleotides away from the protospacer is sufficient for PpCas9 to function.

The majority of Cas nucleases known thus far, which are capable of introducing double-strand breaks into DNA, have complex multi-letter PAM sequences, limiting the choice of sequences suitable for cutting. Among the Cas nucleases studied to date, which recognize short PAMs, only PpCas9 can recognize sequences flanked by the RT motif.

The second advantage of PpCas9 is the small protein size (1055 aa). To date, it is the only small-sized protein studied that has a two-letter RT PAM sequence.

PpCas9 is a novel, small-sized Cas nuclease with a short, easy-to-use PAM that differs from the currently known PAM sequences of other nucleases. The PpCas9 protein cuts various DNA targets with high efficiency, including at 37° C., and can become the basis for a new genomic editing tool.

Although the invention has been described with reference to the disclosed embodiments, those skilled in the art will appreciate that the particular embodiments described in detail have been provided for the purpose of illustrating the present invention and are not be construed as in any way limiting the scope of the invention. It will be understood that various modifications may be made without departing from the spirit of the present invention.

The invention claimed is:

1. A method of forming a double-strand break immediately before the nucleotide sequence 5'-NNNN(A/G)T-3' in a DNA molecule by a protein comprising the amino acid sequence of SEQ ID NO: 1, while a temperature of 35° C. to 45° C. is present in order to form the double-strand break in the DNA molecule.

2. A method for modifying a genomic DNA sequence of a unicellular or multicellular organism, comprising the introduction, into at least one cell of said organism, of an effective amount of: a) either a protein comprising the amino acid sequence of SEQ ID NO: 1, or a nucleic acid encoding the protein comprising the amino acid sequence of SEQ ID NO: 1, and b) either a guide RNA comprising a sequence that forms a duplex with the nucleotide sequence of an organism's genomic DNA region, which is directly adjacent to the nucleotide sequence 5'-NNNN(A/G)T-3' and interacts with said protein following the formation of the duplex, or a DNA sequence encoding said guide RNA;

wherein interaction of said protein with the guide RNA and the nucleotide sequence 5'-NNNN(A/G)T-3' results in the formation of a double-strand break in the genomic DNA sequence immediately adjacent to the sequence 5'-NNNN(A/G)T-3'.

3. The method of claim 2, further comprising the introduction of an exogenous DNA sequence simultaneously with the guide RNA.

* * * * *

SEQUENCE LISTING

<160> NUMBER OF SEQ ID NOS: 27

<210> SEQ ID NO 1

```
<211> LENGTH: 1055
<212> TYPE: PRT
<213> ORGANISM: Pasteurella pneumotropica
<220> FEATURE:
<223> OTHER INFORMATION: protein homologous to Cas9

<400> SEQUENCE: 1

Met Gln Asn Asn Pro Leu Asn Tyr Ile Leu Gly Leu Asp Leu Gly Ile
1               5                   10                  15

Ala Ser Ile Gly Trp Ala Val Val Glu Ile Asp Glu Glu Ser Ser Pro
            20                  25                  30

Ile Arg Leu Ile Asp Val Gly Val Arg Thr Phe Glu Arg Ala Glu Val
        35                  40                  45

Ala Lys Thr Gly Glu Ser Leu Ala Leu Ser Arg Arg Leu Ala Arg Ser
    50                  55                  60

Ser Arg Arg Leu Ile Lys Arg Arg Ala Glu Arg Leu Lys Lys Ala Lys
65                  70                  75                  80

Arg Leu Leu Lys Ala Glu Lys Ile Leu His Ser Ile Asp Glu Lys Leu
                85                  90                  95

Pro Ile Asn Val Trp Gln Leu Arg Val Lys Gly Leu Lys Glu Lys Leu
            100                 105                 110

Glu Arg Gln Glu Trp Ala Ala Val Leu Leu His Leu Ser Lys His Arg
        115                 120                 125

Gly Tyr Leu Ser Gln Arg Lys Asn Glu Gly Lys Ser Asp Asn Lys Glu
    130                 135                 140

Leu Gly Ala Leu Leu Ser Gly Ile Ala Ser Asn His Gln Met Leu Gln
145                 150                 155                 160

Ser Ser Glu Tyr Arg Thr Pro Ala Glu Ile Ala Val Lys Lys Phe Gln
                165                 170                 175

Val Glu Glu Gly His Ile Arg Asn Gln Arg Gly Ser Tyr Thr His Thr
            180                 185                 190

Phe Ser Arg Leu Asp Leu Leu Ala Glu Met Glu Leu Leu Phe Gln Arg
        195                 200                 205

Gln Ala Glu Leu Gly Asn Ser Tyr Thr Ser Thr Thr Leu Leu Glu Asn
    210                 215                 220

Leu Thr Ala Leu Leu Met Trp Gln Lys Pro Ala Leu Ala Gly Asp Ala
225                 230                 235                 240

Ile Leu Lys Met Leu Gly Lys Cys Thr Phe Glu Pro Ser Glu Tyr Lys
                245                 250                 255

Ala Ala Lys Asn Ser Tyr Ser Ala Glu Arg Phe Val Trp Leu Thr Lys
            260                 265                 270

Leu Asn Asn Leu Arg Ile Leu Glu Asn Gly Thr Glu Arg Ala Leu Asn
        275                 280                 285

Asp Asn Glu Arg Phe Ala Leu Leu Glu Gln Pro Tyr Glu Lys Ser Lys
    290                 295                 300

Leu Thr Tyr Ala Gln Val Arg Ala Met Leu Ala Leu Ser Asp Asn Ala
305                 310                 315                 320

Ile Phe Lys Gly Val Arg Tyr Leu Gly Glu Asp Lys Lys Thr Val Glu
                325                 330                 335

Ser Lys Thr Thr Leu Ile Glu Met Lys Phe Tyr His Gln Ile Arg Lys
            340                 345                 350

Thr Leu Gly Ser Ala Glu Leu Lys Lys Glu Trp Asn Glu Leu Lys Gly
        355                 360                 365

Asn Ser Asp Leu Leu Asp Glu Ile Gly Thr Ala Phe Ser Leu Tyr Lys
    370                 375                 380
```

```
Thr Asp Asp Asp Ile Cys Arg Tyr Leu Glu Gly Lys Leu Pro Glu Arg
385                 390                 395                 400

Val Leu Asn Ala Leu Leu Glu Asn Leu Asn Phe Asp Lys Phe Ile Gln
                405                 410                 415

Leu Ser Leu Lys Ala Leu His Gln Ile Leu Pro Leu Met Leu Gln Gly
            420                 425                 430

Gln Arg Tyr Asp Glu Ala Val Ser Ala Ile Tyr Gly Asp His Tyr Gly
        435                 440                 445

Lys Lys Ser Thr Glu Thr Thr Arg Leu Leu Pro Thr Ile Pro Ala Asp
    450                 455                 460

Glu Ile Arg Asn Pro Val Val Leu Arg Thr Leu Thr Gln Ala Arg Lys
465                 470                 475                 480

Val Ile Asn Ala Val Val Arg Leu Tyr Gly Ser Pro Ala Arg Ile His
            485                 490                 495

Ile Glu Thr Ala Arg Glu Val Gly Lys Ser Tyr Gln Asp Arg Lys Lys
            500                 505                 510

Leu Glu Lys Gln Gln Glu Asp Asn Arg Lys Gln Arg Glu Ser Ala Val
            515                 520                 525

Lys Lys Phe Lys Glu Met Phe Pro His Phe Val Gly Glu Pro Lys Gly
            530                 535                 540

Lys Asp Ile Leu Lys Met Arg Leu Tyr Glu Leu Gln Gln Ala Lys Cys
545                 550                 555                 560

Leu Tyr Ser Gly Lys Ser Leu Glu Leu His Arg Leu Leu Glu Lys Gly
                565                 570                 575

Tyr Val Glu Val Asp His Ala Leu Pro Phe Ser Arg Thr Trp Asp Asp
            580                 585                 590

Ser Phe Asn Asn Lys Val Leu Val Leu Ala Asn Glu Asn Gln Asn Lys
            595                 600                 605

Gly Asn Leu Thr Pro Tyr Glu Trp Leu Asp Gly Lys Asn Asn Ser Glu
    610                 615                 620

Arg Trp Gln His Phe Val Val Arg Val Gln Thr Ser Gly Phe Ser Tyr
625                 630                 635                 640

Ala Lys Lys Gln Arg Ile Leu Asn His Lys Leu Asp Glu Lys Gly Phe
                645                 650                 655

Ile Glu Arg Asn Leu Asn Asp Thr Arg Tyr Val Ala Arg Phe Leu Cys
            660                 665                 670

Asn Phe Ile Ala Asp Asn Met Leu Leu Val Gly Lys Gly Lys Arg Asn
        675                 680                 685

Val Phe Ala Ser Asn Gly Gln Ile Thr Ala Leu Leu Arg His Arg Trp
    690                 695                 700

Gly Leu Gln Lys Val Arg Glu Gln Asn Asp Arg His His Ala Leu Asp
705                 710                 715                 720

Ala Val Val Val Ala Cys Ser Thr Val Ala Met Gln Gln Lys Ile Thr
            725                 730                 735

Arg Phe Val Arg Tyr Asn Glu Gly Asn Val Phe Ser Gly Glu Arg Ile
            740                 745                 750

Asp Arg Glu Thr Gly Glu Ile Ile Pro Leu His Phe Pro Ser Pro Trp
        755                 760                 765

Ala Phe Phe Lys Glu Asn Val Glu Ile Arg Ile Phe Ser Glu Asn Pro
    770                 775                 780

Lys Leu Glu Leu Glu Asn Arg Leu Pro Asp Tyr Pro Gln Tyr Asn His
785                 790                 795                 800
```

-continued

```
Glu Trp Val Gln Pro Leu Phe Val Ser Arg Met Pro Thr Arg Lys Met
                805                     810                     815

Thr Gly Gln Gly His Met Glu Thr Val Lys Ser Ala Lys Arg Leu Asn
        820                     825                     830

Glu Gly Leu Ser Val Leu Lys Val Pro Leu Thr Gln Leu Lys Leu Ser
        835                     840                     845

Asp Leu Glu Arg Met Val Asn Arg Asp Arg Glu Ile Ala Leu Tyr Glu
    850                     855                     860

Ser Leu Lys Ala Arg Leu Glu Gln Phe Gly Asn Asp Pro Ala Lys Ala
865                     870                     875                     880

Phe Ala Glu Pro Phe Tyr Lys Lys Gly Gly Ala Leu Val Lys Ala Val
                885                     890                     895

Arg Leu Glu Gln Thr Gln Lys Ser Gly Val Leu Val Arg Asp Gly Asn
        900                     905                     910

Gly Val Ala Asp Asn Ala Ser Met Val Arg Val Asp Val Phe Thr Lys
        915                     920                     925

Gly Gly Lys Tyr Phe Leu Val Pro Ile Tyr Thr Trp Gln Val Ala Lys
        930                     935                     940

Gly Ile Leu Pro Asn Arg Ala Ala Thr Gln Gly Lys Asp Glu Asn Asp
945                     950                     955                     960

Trp Asp Ile Met Asp Glu Met Ala Thr Phe Gln Phe Ser Leu Cys Gln
                965                     970                     975

Asn Asp Leu Ile Lys Leu Val Thr Lys Lys Thr Ile Phe Gly Tyr
                980                     985                     990

Phe Asn Gly Leu Asn Arg Ala Thr Ser Asn Ile Asn Ile Lys Glu His
        995                     1000                    1005

Asp Leu Asp Lys Ser Lys Gly Lys Leu Gly Ile Tyr Leu Glu Val Gly
    1010                    1015                    1020

Val Lys Leu Ala Ile Ser Leu Glu Lys Tyr Gln Val Asp Glu Leu Gly
1025                    1030                    1035                    1040

Lys Asn Ile Arg Pro Cys Arg Pro Thr Lys Arg Gln His Val Arg
                1045                    1050                    1055
```

<210> SEQ ID NO 2
<211> LENGTH: 3168
<212> TYPE: DNA
<213> ORGANISM: Pasteurella pneumotropica
<220> FEATURE:
<223> OTHER INFORMATION: protein homologous to Cas9

<400> SEQUENCE: 2

```
atgcaaaata atccattaaa ttacatttta gggttagatt taggcattgc ttctattggt      60
tgggcggttg tggaaattga tgaggagagt tcacctattc gcttaattga tgtgggcgtc     120
cgtacatttg aacgggctga agtcgctaaa accggcgaaa gtttagcatt gtctcgtcgt     180
ttagctcgtt catcacggcg attaattaaa cgccgagcag agcgattaaa aaaagcaaaa     240
cgtttattaa aagcagaaaa gattttacat tctattgatg aaaaattacc cattaatgtt     300
tggcagcttc gagtaaaagg attgaaggaa aaactcgaac gtcaggagtg ggcagcggtt     360
ttattacatt tgtcaaagca tcgtggctat ttatcacaac gtaaaaatga gggtaaaagt     420
gataataaag agctgggggc attactttca ggtatcgcaa gtaaccacca aatgttgcaa     480
tcctccgaat atcgtacccc tgcagaaatt gcagtcaaaa aatttcaagt agaagaagga     540
catattcgta tcaacgtgg atcttatacc cataccttta gccgtttgga tttgttggca     600
gaaatggaat attatttca acgccaagct gagttaggca attcttacac gtccaccaca     660
```

```
ttattagaaa atttgacggc gttactaatg tggcaaaagc cagctcttgc gggtgatgcg      720
attttaaaaa tgttgggcaa gtgtaccttc gaacccagcg aatataaagc cgcaaaaaat      780
agttattctg ctgaacgttt tgtgtggtta accaagctga ataatttacg cattttagaa      840
aatggcacgg aaagagcttt aaatgacaat gaacgttttg ctttgcttga gcaaccgtat      900
gagaaatcaa aattaactta tgctcaagtg agagcaatgc ttgcgttatc tgataatgct      960
attttcaaag gggttcgtta tttaggcgaa gataaaaaaa cagtagagag caaaactacg     1020
ttgatagaaa tgaagtttta tcatcaaatc cgcaaaacat taggcagtgc agaattaaaa     1080
aaggaatgga atgagttaaa aggcaattcc gatttattag atgagattgg cacggcattt     1140
tcgttgtata aaacggatga tgatatttgc cgttatttag agggaaaact accagaaagg     1200
gtattaaatg cgttattgga aaatttaaat ttcgataaat ttattcaact ttcacttaaa     1260
gccttacacc aaattttacc attgatgctg caagggcaac gttatgatga ggcggtttct     1320
gcgatttatg tgatcatta tggtaaaaaa tcgacagaaa caacccgctt gttgccgact     1380
attcctgccg atgaaatccg aaatcctgtg gtattacgca ccctgaccca agcccgtaaa     1440
gtgatcaatg cggtggtgcg gttatatggt tcgcctgccc gtattcatat tgaaacagcg     1500
agagaagtcg gcaaatctta ccaagatcgt aaaaaacttg aaaaacagca agaagataat     1560
cgtaagcaac gtgaaagtgc ggtcaaaaaa tttaaagaaa tgtttccgca ttttgtgggg     1620
gagccgaaag gtaaagatat tttaaaaatg cgattgtatg agttacaaca agcgaaatgt     1680
ttatattctg gaaaatcttt agaacttcat cgtttgcttg agaaggggta tgtagaagtg     1740
gatcacgctt tgccattttc tcgcacgtgg gatgatagct ttaataataa agtactggtg     1800
cttgccaacg agaaccaaaa taaaggcaat ttaacgcctt atgaatggtt agatggtaaa     1860
aataacagtg agcgttggca acattttgtt gtacgagtac aaaccagcgg tttctcttat     1920
gctaaaaaac aacgcatttt gaaccataaa ttggatgaaa aagggtttat cgaacgtaat     1980
ttaaacgata ctcgctatgt agctcgtttc ttatgtaact ttattgccga taatatgttg     2040
ttggttggta aaggcaagcg aaacgtgttt gcttcaaacg gcaaatcac ggcgttattg     2100 cggcatcgtt ggggcttaca aaaagtgcgt gaacagaatg atcgccacca cgcactggac     2160
gcggttgtgg tggcttgctc tactgtggca atgcaacaaa aaatcactcg atttgtgaga     2220
tataacgaag gaaatgtctt tagcggtgaa cgtatcgatc gtgaaactgg cgagattatt     2280
ccattacatt ttccaagccc ttgggctttt ttcaaagaga atgtggaaat tcgcattttt     2340
agtgaaaatc caaaattgga attagaaaat cgcctgcctg attatccgca atataatcac     2400
gaatgggtgc aaccattgtt tgtttcgaga atgccaaccc gaaaaatgac agggcaaggg     2460
catatggaaa cggtaaaatc cgcaaaacga ttaaatgaag gtttaagtgt gttaaaagtc     2520
cctttaacac aacttaaatt gagtgattta gaacgaatgg ttaatcgtga tcgtgaaatt     2580
gcattgtatg aatccttaaa agcacgttta gagcaatttg gtaacgaccc agccaaagcc     2640
tttgccgaac cattctataa aaagggtggg gcattagtca aagcagtccg attggaacaa     2700
acacaaaaat cggggggtatt agtacgtgat ggtaacggtg ttgcggataa tgcttcaatg     2760
gtacgggttg atgttttttac taaaggtgga aaatatttct tagtgccgat ttatacttgg     2820
caggtagcga aagggatttt accgaatagg gctgcgacac aaggtaaaga tgaaaatgat     2880
tgggatatta tggatgaaat ggctactttc caattttctc tatgtcaaaa tgatctaatt     2940
aaattagtta ccaaaaagaa aacaatcttt ggatattta atggattaaa tagagctact     3000
```

-continued

```
agcaatataa atattaaaga gcatgatcta gataagtcta aagggaaatt aggtatttac     3060
ttagaagttg gtgtaaaact agctatttcc cttgaaaagt accaagtcga cgaactcggc     3120
aaaaatatcc gtccttgtcg tccgactaaa cgacagcacg tgcgttaa                  3168
```

```
<210> SEQ ID NO 3
<211> LENGTH: 36
<212> TYPE: DNA
<213> ORGANISM: Artificial Sequence
<220> FEATURE:
<223> OTHER INFORMATION: Synthesized

<400> SEQUENCE: 3
attatagcac tgcgaaatga aaaagggagc tacaac                                  36
```

```
<210> SEQ ID NO 4
<211> LENGTH: 87
<212> TYPE: DNA
<213> ORGANISM: Artificial Sequence
<220> FEATURE:
<223> OTHER INFORMATION: Synthesized

<400> SEQUENCE: 4
gcgaaatgaa aaacguuguu acaauaagag augaauugcu cgcaaagctc ugccucuuga       60
aauuucgguu ucaagaggca ucuuuuu                                            87
```

```
<210> SEQ ID NO 5
<211> LENGTH: 44
<212> TYPE: RNA
<213> ORGANISM: Artificial Sequence
<220> FEATURE:
<223> OTHER INFORMATION: Synthesized
<220> FEATURE:
<221> NAME/KEY: misc_feature
<222> LOCATION: (1)..(20)
<223> OTHER INFORMATION: n is a, c, g, or u

<400> SEQUENCE: 5
nnnnnnnnnn nnnnnnnnnn guuguagcuc ccuuuucauu ucgc                         44
```

```
<210> SEQ ID NO 6
<211> LENGTH: 374
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (330)..(336)
<223> OTHER INFORMATION: n is a, c, g, or t

<400> SEQUENCE: 6
cccggggtac cacggagaga tggtggaaat catctttctc gtgggcatcc ttgatggcca       60
cctcgtcgga agtgcccacg aggatgacag caatgccaat gctggggggg ctcttctgag      120
aacgagctct gctgcctgac acggccagga cggccaacac caaccagaac ttgggagaac      180
agcactccgc tctgggcttc atcttcaact cgtcgactcc ctgcaaacac aaagaaagag      240
catgttaaaa taggatctac atcacgtaac ctgtcttaga agaggctaga tactgcaatt      300
caaggacctt atctcctttc attgagcacn nnnnnnaact ccatctacca gcctactctc      360
ttatctctgg tatt                                                        374
```

```
<210> SEQ ID NO 7
<211> LENGTH: 87
```

```
<212> TYPE: DNA
<213> ORGANISM: Artificial Sequence
<220> FEATURE:
<223> OTHER INFORMATION: Synthesized

<400> SEQUENCE: 7
gcgaaatgaa aaacguuguu acaauaagag augaauuucu cgcaaagcuc ugccucuuga      60
aauuucgguu ucaagaggca ucuuuuu                                         87

<210> SEQ ID NO 8
<211> LENGTH: 45
<212> TYPE: RNA
<213> ORGANISM: Artificial Sequence
<220> FEATURE:
<223> OTHER INFORMATION: Synthesized

<400> SEQUENCE: 8
uaucuccuuu cauugagcac guuguagcuc ccuuuuucau uucgc                     45

<210> SEQ ID NO 9
<211> LENGTH: 374
<212> TYPE: DNA
<213> ORGANISM: Artificial Sequence
<220> FEATURE:
<223> OTHER INFORMATION: Synthesized

<400> SEQUENCE: 9 cccgggtac cacggagaga tggtggaaat catctttctc gtgggcatcc ttgatggcca      60
cctcgtcgga agtgcccacg aggatgacag caatgccaat gctggggggg ctcttctgag     120
aacgagctct gctgcctgac acggccagga cggccaacac caaccagaac ttgggagaac     180
agcactccgc tctgggcttc atcttcaact cgtcgactcc ctgcaaacac aaagaaagag     240
catgttaaaa taggatctac atcacgtaac ctgtcttaga agaggctaga tactgcaatt     300
caaggacctt atctcctttc attgagcacc aacattaact ccatctacca gcctactctc     360
ttatctctgg tatt                                                      374

<210> SEQ ID NO 10
<211> LENGTH: 19
<212> TYPE: DNA
<213> ORGANISM: Artificial Sequence
<220> FEATURE:
<223> OTHER INFORMATION: Synthesized

<400> SEQUENCE: 10
tatctccttc attgagcac                                                  19

<210> SEQ ID NO 11
<211> LENGTH: 20
<212> TYPE: DNA
<213> ORGANISM: Artificial Sequence
<220> FEATURE:
<223> OTHER INFORMATION: Synthesized

<400> SEQUENCE: 11
cagctgaagt aatgttagag                                                 20

<210> SEQ ID NO 12
<211> LENGTH: 20
<212> TYPE: DNA
<213> ORGANISM: Artificial Sequence
<220> FEATURE:
<223> OTHER INFORMATION: Synthesized
```

-continued

```
<400> SEQUENCE: 12
aataagaaaa acattattat                                                     20

<210> SEQ ID NO 13
<211> LENGTH: 20
<212> TYPE: DNA
<213> ORGANISM: Artificial Sequence
<220> FEATURE:
<223> OTHER INFORMATION: Synthesized

<400> SEQUENCE: 13
ggggctataa gtacacaagc                                                     20

<210> SEQ ID NO 14
<211> LENGTH: 20
<212> TYPE: DNA
<213> ORGANISM: Artificial Sequence
<220> FEATURE:
<223> OTHER INFORMATION: Synthesized

<400> SEQUENCE: 14
cgttctcaga agagcccccc                                                     20

<210> SEQ ID NO 15
<211> LENGTH: 20
<212> TYPE: DNA
<213> ORGANISM: Artificial Sequence
<220> FEATURE:
<223> OTHER INFORMATION: Synthesized

<400> SEQUENCE: 15
cccacgagaa agatgatttc                                                     20

<210> SEQ ID NO 16
<211> LENGTH: 136
<212> TYPE: DNA
<213> ORGANISM: Artificial Sequence
<220> FEATURE:
<223> OTHER INFORMATION: Synthesized

<400> SEQUENCE: 16
uaucuccuuu cauugagcac guuguagcuc ccuuuuucau uucgcgaaag cgaaaugaaa         60
aacguuguua caauaagaga ugaauuucuc gcaaagctct gccucuugaa auuucgguuu        120
caagaggcau cuuuuu                                                        136

<210> SEQ ID NO 17
<211> LENGTH: 159
<212> TYPE: RNA
<213> ORGANISM: Artificial Sequence
<220> FEATURE:
<223> OTHER INFORMATION: Synthesized

<400> SEQUENCE: 17
uaucuccuuu cauugagcac guuguagcuc ccuuuuuuca uuucgcagug cuauaaugaa         60
aauuauagca cugcgaaaug aaaaacguug uuacaauaag agaugaauuu cucgcaaagc        120
ucugccucuu gaaauuucgg uuucaagagg caucuuuuu                              159

<210> SEQ ID NO 18
<211> LENGTH: 20
<212> TYPE: DNA
<213> ORGANISM: Artificial Sequence
<220> FEATURE:
<223> OTHER INFORMATION: Synthesized
```

<400> SEQUENCE: 18
tatctccttt cattgagcac                                                   20

<210> SEQ ID NO 19
<211> LENGTH: 375
<212> TYPE: DNA
<213> ORGANISM: Artificial Sequence
<220> FEATURE:
<223> OTHER INFORMATION: Synthesized

<400> SEQUENCE: 19
cccggggtac cacggagaga tggtggaaat catctttctc gtgggcatcc ttgatggcca      60
cctcgtcgga agtgcccacg aggatgacag caatgccaat gctggggggg ctcttctgag     120
aacgagctct gctgcctgac acggccagga cggccaacac caaccagaac ttgggagaac     180
agcactccgc tctgggcttc atcttcaact cgtcgactcc ctgcaaacac aaagaaagag     240
catgttaaaa taggatctac atcacgtaac ctgtcttaga agaggctaga tactgcaatt     300
caaggacctt atctcctttc attgagcacc aacattcaac tccatctacc agcctactct     360
cttatctctg gtatt                                                      375

<210> SEQ ID NO 20
<211> LENGTH: 17
<212> TYPE: PRT
<213> ORGANISM: Artificial Sequence
<220> FEATURE:
<223> OTHER INFORMATION: Synthesized

<400> SEQUENCE: 20

Met Ala Pro Lys Lys Lys Arg Lys Val Gly Ile His Gly Val Pro Ala
1               5                   10                  15

Ala

<210> SEQ ID NO 21
<211> LENGTH: 16
<212> TYPE: PRT
<213> ORGANISM: Artificial Sequence
<220> FEATURE:
<223> OTHER INFORMATION: Synthesized

<400> SEQUENCE: 21

Lys Arg Pro Ala Ala Thr Lys Lys Ala Gly Gln Ala Lys Lys Lys Lys
1               5                   10                  15

<210> SEQ ID NO 22
<211> LENGTH: 20
<212> TYPE: DNA
<213> ORGANISM: Artificial Sequence
<220> FEATURE:
<223> OTHER INFORMATION: Synthesized

<400> SEQUENCE: 22
cagctgaagt aatgttagag                                                  20

<210> SEQ ID NO 23
<211> LENGTH: 250
<212> TYPE: DNA
<213> ORGANISM: Artificial Sequence
<220> FEATURE:
<223> OTHER INFORMATION: Synthesized

<400> SEQUENCE: 23

-continued

```
gagggcctat ttcccatgat tccttcatat ttgcatatac gatacaaggc tgttagagag        60
ataattggaa ttaatttgac tgtaaacaca aagatattag tacaaaatac gtgacgtaga       120
aagtaataat ttcttgggta gtttgcagtt ttaaaattat gttttaaaat ggactatcat       180
atgcttaccg taacttgaaa gtatttcgat ttcttggctt tatatatctt gtggaaagga       240
cgaaacaccg                                                              250
```

```
<210> SEQ ID NO 24
<211> LENGTH: 136
<212> TYPE: DNA
<213> ORGANISM: Artificial Sequence
<220> FEATURE:
<223> OTHER INFORMATION: Synthesized

<400> SEQUENCE: 24
cagctgaagt aatgttagag gttgtagctc cctttttcat ttcgcgaaag cgaaatgaaa        60
aacgttgtta caataagaga tgaatttctc gcaaagctct gcctcttgaa atttcggttt       120
caagaggcat cttttt                                                       136
```

```
<210> SEQ ID NO 25
<211> LENGTH: 29
<212> TYPE: DNA
<213> ORGANISM: Artificial Sequence
<220> FEATURE:
<223> OTHER INFORMATION: Synthesized

<400> SEQUENCE: 25
agttcctgga tagaggaaag taactcgtg                                          29
```

```
<210> SEQ ID NO 26
<211> LENGTH: 11
<212> TYPE: DNA
<213> ORGANISM: Artificial Sequence
<220> FEATURE:
<223> OTHER INFORMATION: Synthesized

<400> SEQUENCE: 26
ttgaggtaga t                                                            11
```

```
<210> SEQ ID NO 27
<211> LENGTH: 87
<212> TYPE: RNA
<213> ORGANISM: Artificial Sequence
<220> FEATURE:
<223> OTHER INFORMATION: Synthesized

<400> SEQUENCE: 27
uuuucacgga gaacuuuggc uuuaaaguuc uccgucucga aacgcucuuu aaguagagag        60
aauaacauug uugcaaaaag uaaagcg                                            87
```